United States Patent [19]  
Young et al.

[11] Patent Number: 4,617,407  
[45] Date of Patent: Oct. 14, 1986

[54] LEUKOTRIENE ANTAGONISTS

[75] Inventors: Robert N. Young, Senneville; Joshua Rokach, Laval, both of Canada

[73] Assignee: Merck Frosst Canada, Inc., Kirkland, Canada

[21] Appl. No.: 645,595

[22] Filed: Aug. 30, 1984

[51] Int. Cl.$^4$ ............... C07D 307/88; C07D 311/04
[52] U.S. Cl. ...................... 549/462; 514/469; 514/460; 514/222; 548/252; 548/253; 548/254; 549/9; 549/52; 549/58; 549/53; 549/399; 549/407; 549/466; 549/467; 549/469; 549/405; 549/406; 549/350
[58] Field of Search ............. 549/399, 466, 462, 467, 549/470, 468, 9, 350, 52, 366, 58, 510, 511, 53; 548/253

[56] References Cited  
U.S. PATENT DOCUMENTS 4,237,144 12/1980 Cragoe, Jr. .................. 549/469  
4,401,669 8/1983 Cragoe, Jr. .................. 549/468

OTHER PUBLICATIONS  
Chem. Abst.; 99; 212,252c.

Primary Examiner—Christopher Henderson  
Attorney, Agent, or Firm—Gabriel Lopez; Richard A. Elder; Paul H. Ginsburg

[57] ABSTRACT

Compounds having the formula:

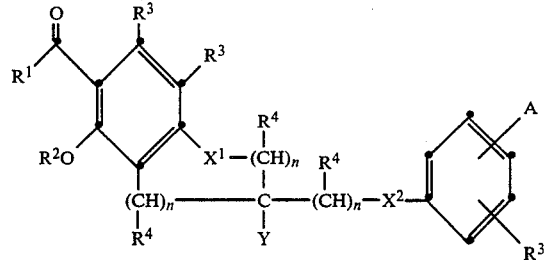

are antagonists of leukotrienes of $C_4$, $D_4$ and $E_4$, the slow reacting substance of anaphylaxis. These compounds are useful as anti-asthmatic, anti-allergic, anti-inflammatory and cytoprotective agents.

3 Claims, No Drawings

LEUKOTRIENE ANTAGONISTS

This invention is directed to compounds which act as antagonists of the leukotrienes.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. The leukotrienes are also thought to be regulators of mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma.

Psoriasis is a human skin disease which effects between two and six percent of the population. There is no adequate therapy for psoriasis and related skin conditions. The evidence for leukotriene involvement in these diseases is as follows. One of the earliest events in the development of preparpillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function. See for example, B. Samuelsson, *Science*, 220 568 (1983).

Several classes of compounds exhibit ability to antagonize the action of leukotrienes in mammals, especially humans. See for example: Great Britain Patent Specification No. 2,058,785; and European Patent Application Nos. 56,172 and 61,800.

The compounds of the present invention may be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The present invention provides compounds that act as antagonists to prevent leukotriene action or as inhibitors to prevent synthesis. This invention further provides compounds which prevent or reverse leukotriene action or prevent leukotriene synthesis when administered orally. This invention also provides compounds which prevent or reverse leukotriene action or prevent leukotriene synthesis when administered by insufflation, intravenously, rectally, topically, parenterally including subcutaneously and intramuscularly, or nasally. This invention also provides methods for the preparation of these compounds. This invention provides intermediates useful in the synthesis of these compounds. Finally, this invention provides pharmaceutical formulations for administering these compounds.

The present invention relates to compounds having activity as leukotriene antagonists, to methods for their preparation, to intermediates useful in their preparation and to methods for using these compounds. Because of their activity as leukotriene antagonists, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems.

The compounds of the present invention are compounds of the formula I:

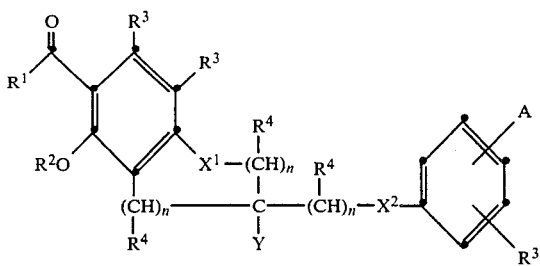

and the pharmaceutically acceptable salts and acid addition salts thereof, wherein:

each n is independently 0, 1, 2 or 3;

$X^1$ and $X^2$ are each independently O, S, SO, $SO_2$ or a bond;

Y is H, OH, alkyl of 1 to 6 carbon atoms which may be straight chain or branched or alkoxy of 1 to 6 carbon atoms which may be straight chain or branched;

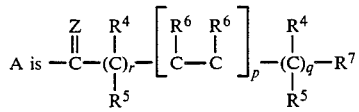

wherein

Z is O; S; H/OH; H/H; $CH_2$; alkenyl of 2 to 4 carbon atoms; or $N-R_8$;

r and q are each independently 0 to 20 provided that the total of r and q does not exceed 20; and p is 0 or 1; and the broken line represents an optional double bond;

$R^1$ is H, alkyl of 1 to 6 carbon atoms which may be straight chain or branched; or alkoxy of 1 to 6 carbon atoms which may be straight chain or branched;

$R^2$ is H, alkyl of 1 to 6 carbon atoms which may be straight chain or branched; $R^4CO-$; or $R^4OCH_2-$;

each $R^3$ is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen (i.e. fluorine, chlorine, bromine or iodine); benzyl; phenethyl; halogen, amino; $N(R^4)_2$; $COOR^4$; $CH_2OR^4$; formyl; CN; trifluoromethylthio; or nitro;

each $R^4$ is independently H or alkyl of 1 to 6 carbon atoms which may be straight chain or branched;

each $R^5$ is independently H, OH, or alkyl of 1 to 6 carbon atoms;

each $R_6$ is independently H, or alkyl of 1 to 4 carbon atoms;

$R_7$ is $COOR^4$; $CH_2OH$; CHO; tetrazole; $CO-NH-SO_2R^8$; $NHSO_2R_8$; hydroxymethylketone; CN; $CON(R^4)_2$; a monocyclic or bicyclic heterocyclic ring containing an acidic hydroxyl group; or

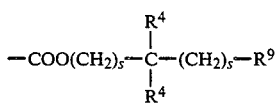

wherein each s is independently 0 to 3; $R^9$ is (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or (B) the radical $W-R^{10}$ wherein W is O, S or NH and $R^{10}$ contains up to 21 carbon atoms and is (1) a hydrocarbon radical or (2) an acyl radical of an organic acyclic or monocyclic carboxylic acid containing not more than 1 heteroatom in the ring; and $R^8$ is $OR^4$; $N-(R^4)_2$; alkyl of 1 to 6 carbon atoms; phenyl or phenyl substituted by alkyl or alkoxy groups of 1 to 3 carbon atoms, halogen, hydroxy, haloalkyl of 1 to 6 carbon atoms, COOH, CN, formyl or acyl of 1 to 6 carbon atoms.

A preferred embodiment of the present invention relates to compounds of Formula Ia:

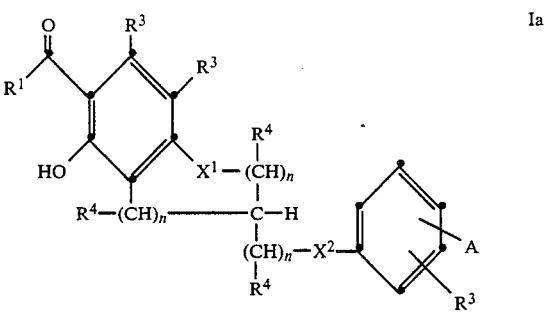

and the pharmaceutically acceptable salts and acid addition salts thereof, wherein:

each n is independently 0, 1 or 2;

$X^1$ and $X^2$ are each independently O, S, SO or $SO_2$;

A is

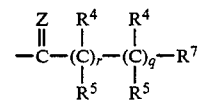

wherein

Z is O; H/OH; H/H; $CH_2$; or $N-R^8$;

r and q are each independently 0 to 5;

$R^1$ is alkyl of 1 to 6 carbon atoms which may be straight chain or branched;

$R^7$ is $COOR^4$, $CH_2OH$, CHO, tetrazole, 8, CN or $CON(R )2$; and $CONHSO_2R^8$, CN or $CON(R^4)_2$; and $R^8$ is $OR^6$, $N(R^4)_2$-alkyl of 1 or 6 carbon atoms, or CN; and $R^3$, $R^4$, $R^5$ and $R^6$ are as defined for Formula I.

A more preferred embodiment of the present invention relates to compounds of Formula Ib:

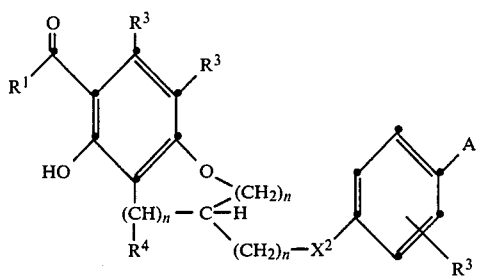
and the pharmaceutically acceptable salts and addition salts thereof;
wherein:
each n is independently 0, 1 or 2;
$X^2$ is O or S;
A s
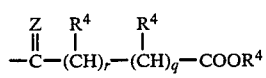
wherein
Z is O; H/OH or H/H;
r and q are each independently 0 to 3;
$R^1$ is as defined for Formula Ia;
$R^3$ is H, alkyl of 1 to 6 carbon atoms which may be straight chain or branched, or halogen;
$R^4$ is as defined for Formula I.
SCHEME I
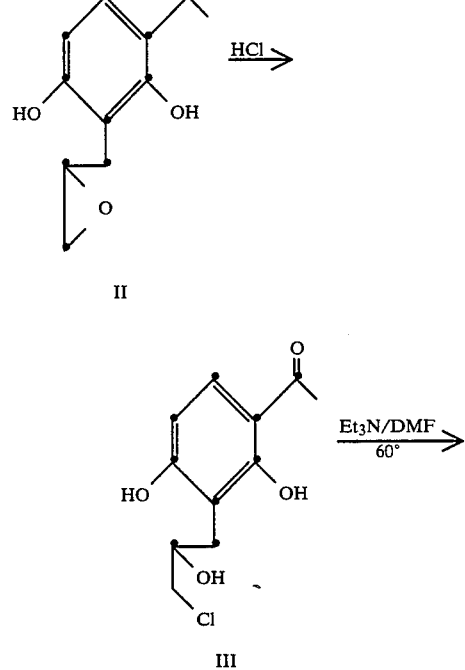
-continued
SCHEME I
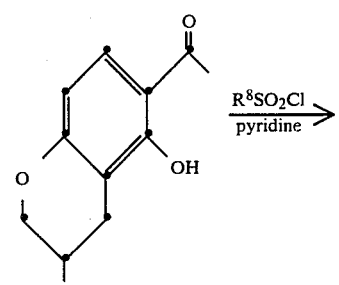
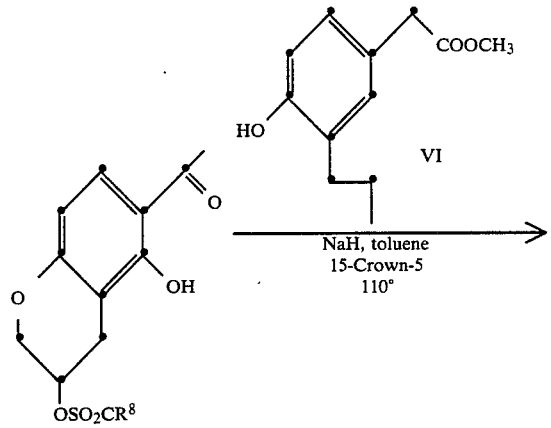
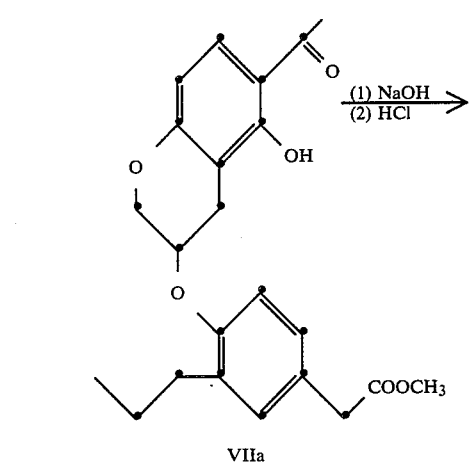

-continued
SCHEME I

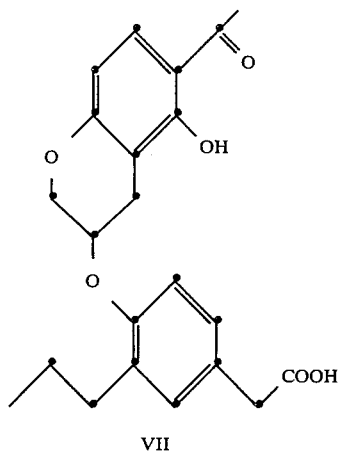

VII

The compounds of the present invention may be prepared by several different routes. According to one method, illustrated in Scheme I, the epoxide II is treated with concentrated hydrochloric acid at room temperature to provide the chlorohydrin (III) which is heated at 30°–80° C. in DMF in the presence of a base such as triethylamine, triton-B or sodium hydride to give the cyclic ether (IV). The alcohol (IV) is reacted in pyridine at controlled low temperature (−10° to +20° C.) with methanesulfonyl chloride or a similar alkyl or arylsulfonyl halide to provide the sulfonic ester (V) which is reacted with the phenol (VI) in an anhydrous solvent such as toluene in the presence of a base such as sodium hydride in the presence of 15-crown-5 with heating at 60°–120° to give the ether (VIIa). The ether (VIIa) is saponified with an aqueous base such as sodium hydroxide. Acidification gives the acid (VII).

SCHEME II

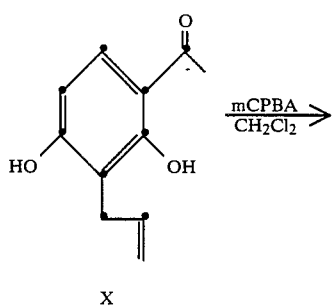

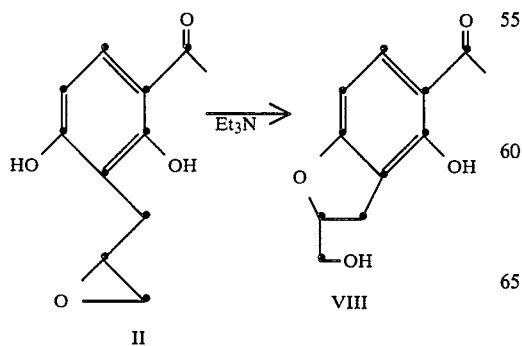

-continued
SCHEME II

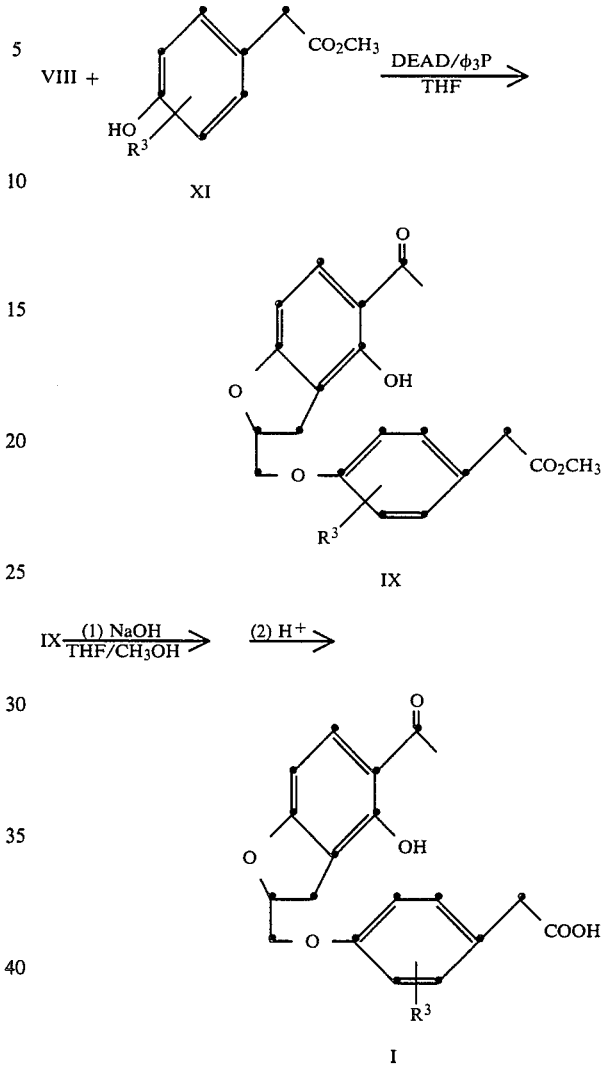

As shown in Scheme II, the olefin X is epoxidized with an equivalent of an oxidizing agent such as m-CPBA in a solvent such as chloroform or dichloromethane at 0°–20° C. to give the epoxide (II) which when treated in a solvent such as ethyl acetate in the presence of a base such as triethylamine at ambient temperature gives the alcohol (VIII). Reaction of the alcohol (VIII) and the phenol (XI) in an anhydrous solvent such as THF in the presence of a dehydrating agent such as DEAD (diethylazodicarboxylate)/Ph$_3$P (Ph represents phenyl) to give the ether (IX) which after saponification and acidification gives the acid (I).

SCHEME III

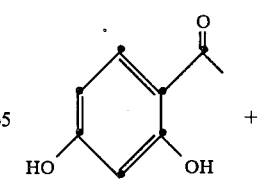

+

-continued
SCHEME III
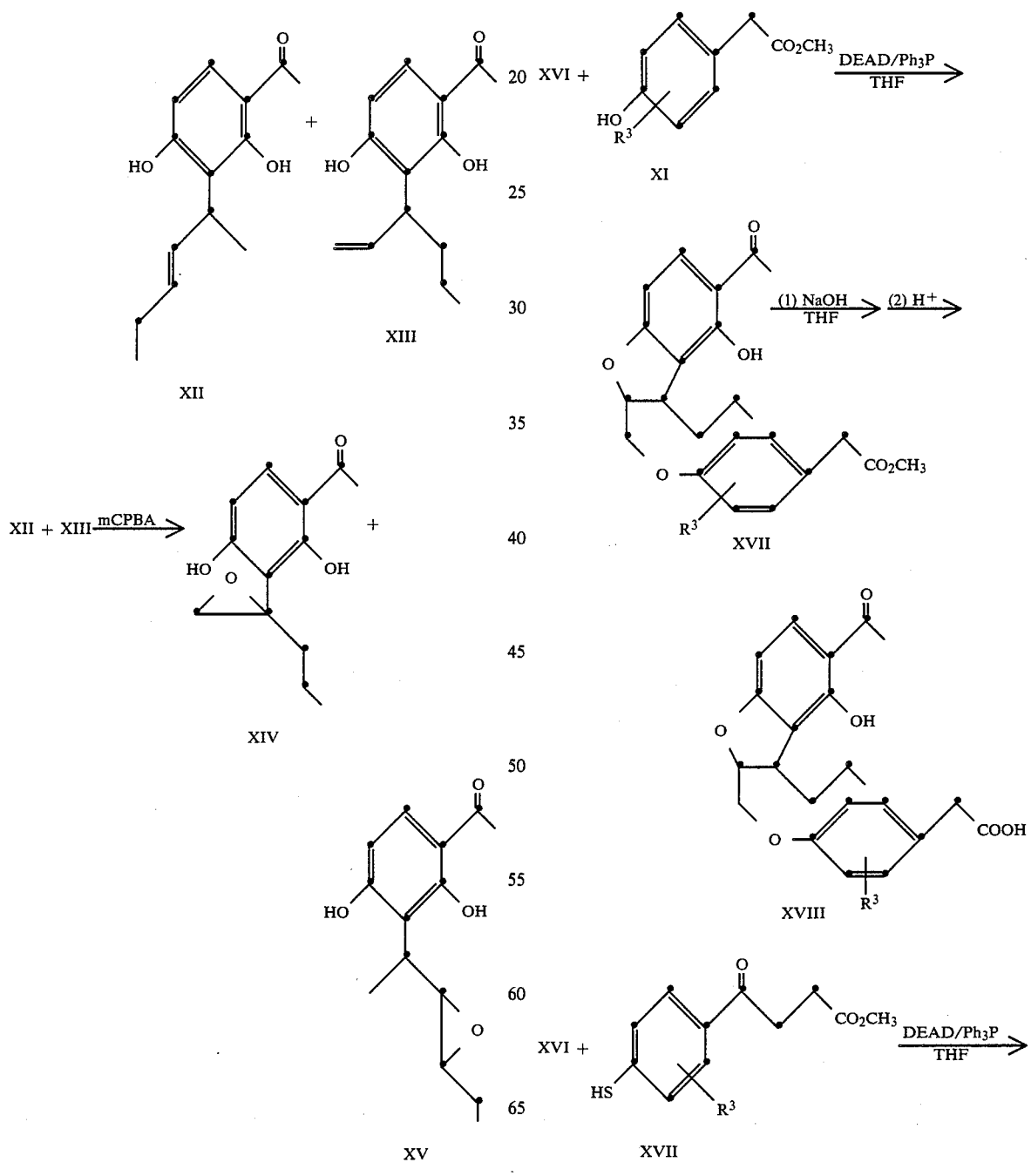

-continued
SCHEME III

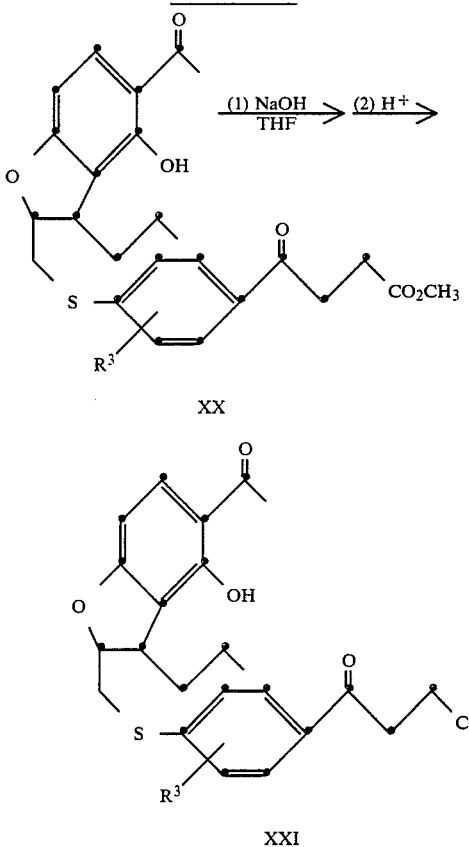

As shown in Scheme III, 2, 4-dihydroxyacetophenone is reacted with a allylic alcohol such as 2-hexenol in an anhydrous solvent such as THF in the presence of a dehydrating agent such as DEAD/Ph₃P to give the ether (XI). Heating the ether (XI) at 180°-220° C. in a basis solvent such as collidine gives a mixture of olefins (XII and XIII), which is not separated but is oxidized as such with an agent such as m-CPBA at 0°-20° C. in a solvent such as chloroform or dichloromethane to give a mixture of epoxides (XVI and XV) which is treated as such in an inert solvent such as ethyl acetate in the presence of a base such as triethylamine at ambient temperature to give a mixture of cyclic ethers from which the ether alcohol (XVI) is isolated by HPLC. The ether alcohol (XVI) is reacted with a phenol (XI) in an inert solvent such as THF with a dehydrating agent such as DEAD/Ph₃P to provide the ether (XVII) which on saponification and acidification gives the acid (XVIII). The alcohol (XVI) can also be reacted with a thiophenol such as (XIX) in the presence of DEAD/Ph₃P to provide the thioether (XX) which is saponified and acidified to provide the acid (XXI).

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer Assay

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The magnitude of a prophylactic or therapeutic dose of a compound of formula I will, of course, vary with the nature of the severity of the condition to be treated and with the particular compound of formula I and its route of administration. In general, the daily dose range for anti-asthmatic, anti-allergic or anti-inflammatory use lies within the range of from about 0.01 mg to about 100 mg per kg body weight of a mammal.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal antiinflammatory drug that might otherwise cause such damage (for example, indomethacin).

The effective daily dosage level for compounds of Formulae I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts"

refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.01 mg to about 20 mg (preferably from about 0.1 mg to about 10 mg) of a compound of formula I per kg of body weight per day and for cytoprotective use from about 0.002 mg to about 100 mg (preferably from about 0.02 mg to about 30 mg and more preferably from about 0.1 mg to about 10 mg) of a compound of Formula I per kg of body weight per day. In the case where an oral composition is employed, a suitable dosage range for anti-asthmatic, anti-inflammatory or anti-allergic use is, e.g. from about 1 to about 100 mg of a compound of formula I per kg of body weight per day, preferably from about 5 mg to about 40 mg per kg and for cytoprotective use from about 0.01 mg to about 100 mg (preferably from about 0.1 mg to about 30 mg and more preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene antagonists of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the leukotriene antagonists of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the compounds of Formula I:

| Injectable Suspension | mg/ml |
|---|---|
| Compound of Formula I | 2.0 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of | 1 ml |

| Tablet | mg/tablet |
|---|---|
| Compound of Formula I | 25.0 |
| Microcrystalline Cellulose | 325.0 |
| Providone | 14.0 |
| Microcrystalline Cellulose | 90.0 |
| Pregelatinized Starch | 43.5 |
| Magnesium Stearate | 2–2.5 |
|  | 500 |

-continued

| Capsule | mg/capsule |
| --- | --- |
| Compound of Formula I | 25.0 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na³⁰ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structually related acetic acid derivatives having similar analgesic and antiinflammatory properties are also intended to be encompassed by this group.

Thus, "acetic acid derivatives" as defined herein are non-narcotic analgesics/non-steroidal antiinflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

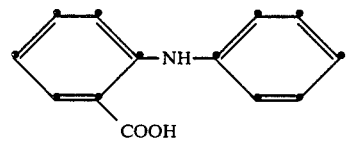

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/nonsteroidal anti-inflammatory drugs which contain the basic structure:

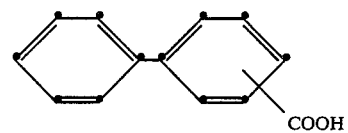

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

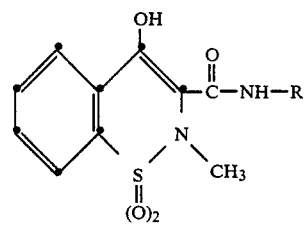

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITCl, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent applications Ser. No. 539,342, filed Oct. 5, 1983, now abandoned, Ser. No. 459,924, filed Jan. 21, 1983, now abandoned, Ser. No. 539,215, filed Oct. 5, 1983, now abandoned, and Ser. No. 547,161, filed Oct. 31, 1983, now abandoned, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983, now abandoned, which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP No. 81102976.8 and like compounds, such as those disclosed in U.S. Pat. Nos. 4,283,408; 4,362,736; 4,394,508; European Patent Application No. 40,696 and a pending application, U.S. Ser. No. 301,616, filed Sept. 14, 1981, now abandoned. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The following examples illustrate the present invention without, however, limiting the same thereto. All temperatures are expressed in degrees Celsius. As used herein, the NMR abbreviations are as follows: s, singlet; d, doublet; t, triplet; q, quartet; qu, quintet; x, sextet; dd, doublet of doublets; and m, multiplet.

EXAMPLE 1

2,4-Dihydroxy-3-(2,3-epoxypropyl)acetophenone 2,4-Dihydroxy-3-(2-propenyl)acetophenone, (10 g, 0.052 moles) was taken up in $CH_2Cl_2$ (1 liter) to which was added mCPBA (85%, 11.6 g). The reaction was stirred at room temperature. After 2 hours another 2 g mCPBA was added and stirring was continued overnight. $Ca(OH)_2$ (8 g) was then added and the mixture was stirred for 15 minutes and then filtered. The filtrate was concentrated to afford the title compound, m.p.: 85° (dec.).

EXAMPLE 2

2-Hydroxymethyl-4-hydroxy-5-acetyl-2,3-dihydrobenzo[[b]furan

The crude compound from Example 1 (8 g) was dissolved in ethyl acetate (250 ml) to which was added 25 ml $Et_3N$ and the mixture was stirred at room temperature overnight. The reaction mixture was concentrated and purified by chromatography on a silica gel column to provide the title compound.

Analysis, calculated: C, 63.46; H, 5.81. Found: C, 63.49; H, 5.84.

EXAMPLE 3

2-(4-(2-Methoxy-2-oxoethyl)phenoxymethyl-4-hydroxy-5-acetyl-2,3-dihydrobenzo[b]furan The compound of Example 2 (1.2 g, 5.763 mmoles) was combined with methyl 4-hydroxyphenylacetate (960 mg) in 60 ml dry THF. To this solution was added DEAD (1.36 ml). This mixture was stirred 20 minutes at room temperature. Triphenylphosphine, (2.27 g) in THF (30 ml) was added dropwise to the above reaction. The reaction mixture was stirred for 60 minutes at room temperature. Then it was warmed to 50° C. and maintained at that temperature overnight. The reaction mixture was concentrated, taken up in 10/1 toluene/ethyl acetate and the insoluble triphenylphosphine oxide was filtered off. The filtrate was purified on HPLC to yield the title compound.

NMR (90 MHz, $CDCl_3$/TMS): 2.5 (3H, m), 3.2 (4H, m), 3.6 (2H, s), 3.7 (3H, s), 4.1 (2H, m), 5.2 (1H), 6.5 (1H, d), 7.2 (4H, m), 7.6 (1H, d), 12.2 (1H, s).

EXAMPLE 4

2-(4-Carboxymethylphenoxymethyl)-4-hydroxy-5-acetyl-2,3-dihydrobenzo[b]furan

The compound of Example 3 (500 mg, 1.403 mmoles) was dissolved in a mixture of THF (2 ml) and CH$_3$OH (2 ml) to which was added 1N NaOH (4.0 ml). After two hours, the reaction mixture was concentrated, taken up in a minimum amount of H$_2$O and extracted with CHCl$_3$. The aqueous phase was acidified with HCl and extracted into CHCl$_3$/CH$_3$OH. The organic extract was dried and concentrated to afford the title compound.

Analysis, calculated: C, 66.66; H, 5.30. Found: C, 66.62; H, 5.20.

EXAMPLE 5

2-((2-Propyl-3-hydroxy-4-acetylphenoxy)methyl)-4-hydroxy-5-acetyl-2,3-dihydrobenzo[b]furan The compound of Example 2 (800 mg, 3.84 mmoles) was combined with 2,4-dihydroxy-3-propylacetophenone (740 mg) in 50 ml dry THF. To this solution was added DEAD (0.726 ml). After 5 minutes triphenylphosphine (1.2 g) were added and the reaction mixture was stirred overnight at room temperature. The reaction mixture was concentrated, taken up in 10/1 toluene/ethyl acetate and the insoluble triphenylphosphine oxide was removed by filtration. The residue after concentration was purified on HPLC using 10/1 toluene/ethyl acetate. The title compound was recrystallized from ether, m.p.: 104°–106°.

Analysis, calculated: C, 68.74; H, 6.29. Found: C, 68.94; H, 6.29.

EXAMPLE 6

2-((4-(2-Methoxy-2-oxoethyl)-2-propylphenoxy)methyl)-4-hydroxy-5-acetyl-2,3-dihydrobenzo[b]furan The compound of Example 2 (2.0 g, 9.61 mmoles) was combined with methyl 4-hydroxy-3-propylphenylacetate (2.0 g) in dry THF (80 ml) under N$_2$ at room temperature. DEAD (1.82 ml) was added and the reaction mixture was stirred 15 minutes at room temperature, then cooled. Triphenylphosphine (3.02 g) in THF (40 ml) was added to the reaction mixture. The reaction mixture was warmed to room temperature over 30 minutes and was stirred overnight. The reaction mixture was concentrated, taken up in ethyl acetate and filtered. The crude product was purified on HPLC using 10/1 toluene/ethyl acetate to afford the title compound. NMR (90 MHz CDCl$_3$/TMS): 0.8 (3H, t), 1.6 (2H, m), 2.6 (2H, t), 2.7 (3H, s), 3.4 (2H, m), 3.6 (2H, s), 3.7 (3H, s), 4.2 (2H, d), 5.3 (1H, m), 6.4 (1H, d), 6.8 (1H, d), 7.2 (1H, s), 7.3 (1H, d), 7.6 (1H, d), 12.7 (1H, s).

EXAMPLE 7

2-((4-Carboxymethyl-2-propylphenoxy)methyl)-4-hydroxy-5-acetYl-2,3-dihydrobenzo[b]furan The compound of Example 6 (600 mg, 1.51 mmoles) was taken up in THF (5 ml) to which was added 1N NaOH (4 ml). The reaction mixture was stirred at room temperature. The THF was removed in vacuo and the residue was diluted with H$_2$O and extracted with CHCl$_3$. The aqueous phase was acidified with conc. HCl and extracted with CHCl$_3$. The organic extract was dried and concentrated in vacuo. The title compound was crystallized from ether/hexane.

Analysis, calculated: C, 68.74; H, 6.29. Found: C, 68.74; H, 6.08.

EXAMPLE 8

3,5-Dihydroxy-6-acetyl-2,3-dihydro-4H-benzo[b]pyran

Step 1:

2,4-Dihydroxy-3-(2-hydroxy-3-chloropropyl)-acetophenone

The epoxide from Example 1 (1 g) was dissolved in dioxane (2 ml) and concentrated HCl (1 ml). After 1 hour at ambient temperature, the mixture was poured into brine and extracted with ethyl acetate. The organic extract was dried over Na$_2$SO$_4$ and reduced to dryness to give the crude title compound which was used as such in the next step.

Step 2:

A mixture of 2,4-dihydroxy-3-(2-hydroxy-3-chloropropyl)acetophenone (2.7 g) and triethylamine (5 ml) in dry DMF (50 ml) was heated to 60° under nitrogen. After two hours, the solvent was removed in vacuo and the residue was partitioned between ethyl acetate and water. The aqueous phase was acidified with 6N hydrochloric acid and extracted into ethyl acetate. The combined organics were dried and evaporated to afford the title compound which was recrystallized from ethyl acetate-hexane, m.p. 130°–132°.

EXAMPLE 9

6-Acetyl-5-hydroxy-3-methanesulfonyl-2,3-dihydro[4H]-benzo[b]pyran

The compound of Example 8 (250 mg) was dissolved in dry pyridine (5 ml) and cooled to 0°. Methanesulfonylchloride (100 μl) was added to the stirred solution, which warmed to room temperature and stirred for 16 hours. The pyridine was removed in vacuo and the residue was partitioned between ethyl acetate and water. The organic phase was washed with dilute acid, water, dried and evaporated to afford the title compound, m.p. 158°–162°.

EXAMPLE 10

6-Acetyl-5-hydroxy-3-(4-(2-methoxy-2-oxoethyl)-2-propylphenoxy)-2,3-dihydro[4H]benzo[b]pyran The compound of Example 9 (1.13 g), methyl 4-hydroxy-3-propylphenylacetate (800 mg) and sodium hydride (59%, 320 mg) in dry toluene (50 ml) were stirred at room temperature under nitrogen for 30 minutes in an ultrasonic bath. 15-Crown-5 (about 1.5 ml) was added slowly until hydrogen evolution ceased. The reaction mixture was then heated at 110° for 15 minutes. The reaction was cooled to room temperature and poured into a mixture of ice and 1N HCl. The ice mixture was extracted with ethyl acetate. The combined organic extracts were washed with brine, dried and concentrated in vacuo. The residue was purified by chromatography on silica gel to afford the title compound, m.p. 59°–60°.

Analysis, calculated: C, 69.02; H, 6.58. Found: C, 69.02; H, 6.57.

EXAMPLE 11

6-Acetyl-5-hydroxy-3-(4-carboxymethyl-2-propylphenoxy)-2,3-dihydro[4H]benzo[b]pyran The compound of Example 10 (25 mg) was dissolved in 1N NaOH (0.2 ml) and THF (1 ml). The reaction mixture was stirred at room temperature for 1.5 hours. The reaction was poured into a mixture of ice and dilute HCl and extracted with ethyl acetate. The combined organic extracts were dried and evaporated to yield the title compound which was recrystallized from ether-hexane, m.p. 129°–129.5°.

Analysis, calculated: C, 68.74; H, 6.29. Found: C, 68.79; H, 6.61.

EXAMPLE 12

2-Hydroxy-4-(2-hexenyloxy)acetophenone 2,4-Dihydroxyacetophenone (20 g, 131 moles) and 2-hexen-1-ol (13.2 g) were taken up in dry THF (300 ml) under $N_2$. To this mixture was added DEAD, (24.5 ml). The reaction mixture was then cooled to 0°. Triphenylphosphine (41.4 g) in THF (200 ml) was added dropwise to the cooled solution. The reaction mixture was brought to room temperature and stirred 2 hours. The reaction mixture was concentrated, taken up in ethyl acetate and filtered to remove triphenylphosphine oxide. The residue after concentration in vacuo was purified on a silica gel column to afford the title compound.

NMR (90 MHz, $CDCl_3$/TMS): 0.9 (3H, t), 1.4 (2H, m), 2.1 (2H, q), 2.5 (3H, s), 4.4 (2H, d), 5.7 (2H, m), 6.4 (2H, m), 7.6 (1H, d), 12.7 (1H, s).

EXAMPLE 13

2,4-Dihydroxy-3-(alpha-vinylbutyl)acetophenone

The compound of Example 12 (22 g, 0.094 moles) was taken up in 90 ml collidine and heated to 165°. TLC after about 30 hours still showed starting material. Heating was continued an additional 24 hours. TLC showed that the reaction was almost complete. Heating was continued an additional 10 hours and the reaction was cooled to room temperature overnight. The collidine was removed under high vacuum. The residue was taken up in 600 ml $CHCl_3$ and washed with water, 3×200 ml, 3N HCl, dried and concentrated. Purification of the residue on a silica gel column using 10/3 hexane/ethyl acetate afforded the title compound mixed with an isomeric impurity. The mixture was used as such in the following Example.

EXAMPLE 14

2,3-Dihydroxy-3-(1-propyl-2,3-epoxypropyl)acetophenone

The mixture of Example 13 (20 g, 0.0854 moles) was taken up in 1.5 liters $CH_2Cl_2$ to which was added at 0° mCPBA (85%, 18.2 g). The reaction mixture was stirred at about 5° for 72 hours. The reaction mixture was concentrated and filtered to afford the crude title compound which was used as such in the following Example.

EXAMPLE 15

2-Hydroxymethyl-3-propyl-4-hydroxy-5-acetyl-2,3-dihydrobenzo[b]furan

The compound of Example 14 (22 g, 0.0878 moles) was taken up in 300 ml ethyl acetate to which was added 40 ml $Et_3N$. The reaction mixture was stirred at room temperature overnight. The reaction mixture was concentrated, taken up in $CHCl_3$ and washed with dilute HCl, dried and concentrated. The residue was purified on a silica gel column using 10/3 hexane/ethyl acetate to afford the title compound as a mixture of diastereomers.

NMR ($CDCl_3$) δ: 0.9 (3H, m), 1.0–2.0 (4H, m), 2.51 (3H, s), 3.0–4.1 (4H, m), 4.8 (1H, m), 6.35 (1H, two d), 7.60 (1H, d), 12.7 (1H, two s).

EXAMPLE 16

2-(4-(2-Methoxy-2-oxoethyl)phenoxymethyl)-3-propyl-4-hydroxy-5-acetyl-2,3-dihydroxybenzo[b]furan The compound from Example 15 (1.5 g, 6.0 mmoles), methyl 4-hydroxyphenylacetate (1.1 g, 1.1 equivalent) and 40 ml dry THF were combined under $N_2$ at room temperature. DEAD (1.13 ml) was then added and the reaction mixture was stirred 15 minutes at room temperature. Triphenyl phosphine (1.9 g) in 15 ml THF was then added and the reaction mixture was stirred at room temperature overnight. The reaction mixture was concentrated, taken up in 2/1 hexane/ethyl acetate and filtered to remove the insoluble triphenylphosphine oxide. The residue was purified on a silica gel column using 2/1 toluene/ethyl acetate then repurified on HPLC using 10/1 toluene/ethyl acetate to afford the title compound.

NMR (90 MHz, $CDCl_3$/TMS): 0.9 (3H, m), 1.3 (2H, m), 1.7 (2H, m), 2.6 (3H, s), 3.5 (2h, d), 3.6 (3H, s), 4.1 (1H, m), 4.4 (2H, d), 5.1 (1H, m), 6.4 (1H, q), 6.9 (2H, dd), 7.2 (2H, m), 12.7 (1H, s).

EXAMPLE 17

(2S*,3S* and 2S*,3R*) 2-(4-Carboxymethylphenoxymethyl)-3-propyl-4-hydroxy-5-acetyl-2,3-dihydrobenzo-[b]furan.

The compound from Example 16 (650 mg, 1.63 moles) was taken up in 5 ml THF to which was added 1 N NaOH (4.2 ml). After three hours, the reaction volume wad diluted with $H_2O$ and the THF was removed in vacuo. The aqueous phase was wahsed with $CHCl_3$, then acidified and extracted into $CHCl_3$. The organic extract was dried and concentrated. The residue was triturated with ether to afford the title compound as a white solid which was recrystallized from toluene, m.p.: 104°–106°.

Analysis, calcualted: C, 68.74; H, 6.29. Found: C, 68.71; H, 6.40.

EXAMPLE 18

(2S*,3S* and 2S*,3R*) 2-((4-(1,4-dioxo-4-methoxybutyl)phenylthio)methyl)-3-propyl-4-hydroxy-5-acetyl-2,3-dihydrobenzo[b]furan The compound of Example 15 (1.4 g, 5.59 mmoles, 1 equivalent) and methyl 4-mercapto-γ-oxobenzenebutanoate (1.4 g) was taken up in 30 ml THF. This mixture was added dropwise to a 0° solution of 1.2 equivalent DEAD, (1.1 ml) and 1.2 equivalent (1.76 g) in 40 ml THF. The reaction mixture was stirred cold 30 minutes, then warmed to room temperature. The reaction mixture was stirred at room temperature overnight. The reaction mixture was concentrated, purified on a column of silica gel using 10/1 toluene/ethyl acetate to afford the title compound.

NMR (90 MHz, $CDCl_3$/TMS): 0.9 ppm (3H, t), 1.1 ppm (2H, m), 1.8 ppm (2H, m), 2.5 ppm (3H, s), 2.7 ppm (2H, t), 3.3 ppm (4H, m), 3.4 ppm (1H, m), 3.7 ppm (3H, s), 4.7 (1H, m), 6.6 (1H, dd), 7.2 (1H, d), 7.4 ppm (2H, m), 7.6 ppm (1H, d), 7.9 (1H, dd), 12.7 (1H, s).

EXAMPLE 19

(2S*,3S* and 2S*,3R*)
2((4-(1-oxo-3-carboxypropyl)-phenylthio)methyl)-3-propyl-4-hydroxy-5-acetyl-2,3-dihydrobenzo[b]furan The compound of Example 18 (430 mg, 0.9418 mmoles) was taken up in THF (5.8 ml) to which was added 1N NaOH (2.4 ml) and 2.5 ml $H_2O$. The reaction mixture was stirred at room temperature under $N_2$. After two hours, the THF was removed in vacuo and the reaction mixture was diluted to twice its volume with $H_2O$ and extracted with $CHCl_3$. The aqueous phase was acidified with conc. HCl, extracted into $CHCl_3$ and the organic phase was dried and concentrated. The residue was triturated with ether to afford the title compound, m.p. 110°–112°.

Analysis, calculated: C, 65.15; H, 5.92; S, 7.24. Found: C, 65.08; H, 6.00; S, 7.43.

Claims to the invention follow.
What is claimed is:
1. Compounds having the formula:

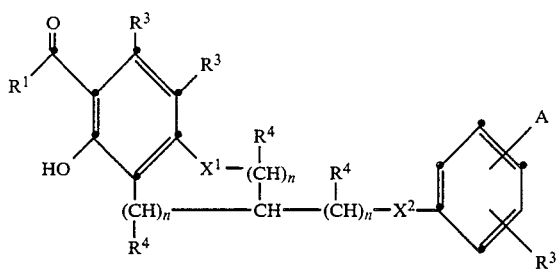

and the pharmaceutically acceptable salts and acid addition salts thereof, wherein:
each n is independently 0 or 1;
$X^1$ is O;
$X^2$ is O or S;

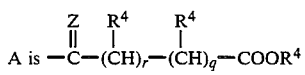

wherein
Z is O or H/H;
r and q are each independently 0 to 2;
$R^1$ is alkyl of 1 to 6 carbon atoms which may be straight chain or branched;
each $R^3$ is independently H or alkyl of 1 to 6 carbon atoms which may be straight chain or branched; and
each $R^4$ is independently H or alkyl of 1 to 6 carbon atoms which may be straight chain or branched.

2. The compounds of claim 1:
2-(4-(2-Methoxy-2-oxoethyl)phenoxymethyl-4-hydroxy-5-acetyl-2,3-dihydrobenzo[b]furan;
2-(4-Carboxymethylphenoxymethyl)-4-hydroxy-5-acetyl-2,3-dihdrobenzo[b]furan;
2-((4-(2-Methoxy-2-oxoethyl)-2-propylphenoxy)methyl)-4-hydroxy-5-acetyl-2,3-dihydrobenzo[b]furan;
2-((4-Carboxymethyl-2-propylphenoxy)methyl)-4-hydroxy-5-acetyl-2,3-dihydrobenzo[b]furan;
6-Acetyl-5-hydroxy-3-(4-(2-methoxy-2-oxoethyl)-2-propylphenoxy)-2,3-dihydro[4H]benzo[b]pyran;
6-Acetyl-5-hydroxy-3-(4-carboxymethyl-2-propylphenoxy)-2,3-dihydro[4H]benzo[b]pyran;
2-(4-(2-Methoxy-2-oxoethyl)phenoxymethyl)-3-propyl-4-hydroxy-5-acetyl-2,3-dihydroxybenzo[b]furan;
(2S*,3S*) 2-(4-Carboxymethylphenoxymethyl)-3-propyl-4-hydroxy-5-acetyl-2,3-dihydrobenzo[b]furan;
(2S*,3R*) 2-(4-carboxymethylphenoxymethyl)-3-propyl-4-hydroxyl-5-acetyl-2,3-dihydrobenzo[b]furan;
(2S*,3S*) 2-((4-(1-oxo-3-carboxypropyl)phenylthio)methyl)-3-propyl-4-hydroxyl-5-acetyl-2,3-dihydrobenzo[b]furan;
(2S*,3R*) 2-((4-(1-oxo-3-carboxypropyl)phenylthio)methyl)-3-propyl-4-hydroxy-5-acetyl-2,3-dihydrobenzo[b]furan;
(2S*,3S*) 2-((4-(1,4-dioxo-4-methoxybutyl)phenylthio)methyl)-3-propyl-4-hydroxy-5-acetyl-2,3-dihyrdobenzo[b]furan; and
(2S*,3R*) 2-((4-(1, 4-dioxo-4-methoxybutyl)phenylthio)methyl)-3-propyl-4-hydroxy-5-acetyl-2,3-dihydrobenzo[b]furan.

3. 2-((2-Propyl-3-hydroxy-4-acetylphenoxy)methyl)-4-hydroxy-5-acetyl-2,3-dihydrobenzo[b]furan.

* * * * *